United States Patent [19]

Yanagida et al.

[11] Patent Number: 5,387,519
[45] Date of Patent: Feb. 7, 1995

[54] RECOMBINANT AVIPOXVIRUS

[75] Inventors: Noboru Yanagida, Kawasaki; Sakiko Saeki, Tokyo; Ryohei Ogawa; Kouichi Kamogawa, both of Yokohama, all of Japan

[73] Assignee: Nippon Zeon Co., Ltd., Tokyo, Japan

[21] Appl. No.: 752,982

[22] Filed: Sep. 3, 1991

Related U.S. Application Data

[63] Continuation of Ser. No. 168,959, Mar. 16, 1988, abandoned.

[30] Foreign Application Priority Data

| Mar. 27, 1987 | [JP] | Japan | 62-73568 |
| Sep. 14, 1987 | [JP] | Japan | 62-229972 |
| Mar. 11, 1988 | [JP] | Japan | 63-57947 |

[51] Int. Cl.⁶ .................. C12N 7/01; C12N 15/39; C12N 15/86
[52] U.S. Cl. .................. 435/235.1; 435/320.1; 536/23.1; 935/32
[58] Field of Search .......... 435/235.1, 320.1, 172.3, 435/69.1; 935/32, 57, 65; 536/27, 24.2, 23.1

[56] References Cited

U.S. PATENT DOCUMENTS 5,174,993 12/1992 Paoletti .................. 424/89

FOREIGN PATENT DOCUMENTS

| 0227414 | 7/1987 | European Pat. Off. |
| 2571060 | 4/1986 | France |
| WOA86/00528 | 1/1986 | WIPO |
| WOA86/05806 | 10/1986 | WIPO |
| WO/88/02022 | 3/1988 | WIPO |

OTHER PUBLICATIONS

Perkus et al., *Virology*, 152, 285 (1986).
Chakrabarti et al., *Mol. Cell. Biol.*, 5, 3403 (1985).
Mackett, M. et al. 1982, *Proc. Natl. Acad. Sci. USA* vol. 79 pp. 7415–7419.
Andrewes, C. et al. 1978, *Viruses of Vertebrates*, 4th edition, Bailliére Tindall, London p. 373.
Vieira & Messing Gene, 19 (1982) 259–268.
Boyle et al., *J. Gen. Virol.* 67, 1591 (1986).
Binns et al., *Israel, J. Vet Med.* 42, 124 (1986).
Panicali et al., *Gene* 47, 193 (1986).
Mackett et al., *J. Gen. Virol* 67, 2067 (1986).

*Primary Examiner*—Richard A. Schwartz
*Assistant Examiner*—Mary E. Mosher
*Attorney, Agent, or Firm*—Armstrong, Westerman, Hattori, McLeland & Naughton

[57] ABSTRACT

A recombinant Avipoxvirus having inserted exogenous DNA in a DNA region non-essential to proliferation of Avipoxvirus is provided. The recombinant Avipoxvirus is produced by inserting a promoter and exogenous DNA capable of expression under its control into a DNA region non-essential to proliferation of Avipoxvirus, utilizing DNA coding for a readily detectable enzyme, or, non-homologous DNA fragment.

8 Claims, 11 Drawing Sheets

E: EcoRI    P: PstI    G: BglII
X: XbaI      B: BamHI
V: EcoRV    H: HindIII
Hc: HincII    C: ClaI
K: KpnI      Xb: XbaI
                 Hp: HpaI

RECOMBINANT AVIPOXVIRUS

This application is a continuation of application Ser. No. 168,959, filed Mar. 16, 1988 now abandoned.

FIELD OF THE INVENTION AND RELATED ART STATEMENT

1. Field of the Invention

The present invention relates to a recombinant Avipoxvirus and more particularly, to a recombinant Avipoxvirus having inserted exogenous DNA into a DNA region non-essential to proliferation of Avipoxvirus and a method for production thereof.

2. Related Art

In recent years, a method of constructing recombinant vaccinia virus having inserted exogenous DNA into vaccinia virus has been developed and there has been proposed a method utilizing recombinant vaccinia virus obtained using, as exogenous DNA, for example, DNA coding for infectious diseases as live vaccine (for example, U.S. Pat. No. 4,603,112, WO 84/02077, WO 85/04810 etc.). According to this method, it is possible to insert a variety of exogenous DNAs depending upon purpose and, the method is expected to be promising as a new process for producing live vaccine.

In vaccinia virus, however, its host range is limited. For this reason, it is almost impossible to apply techniques of recombinant vaccinia virus to production of, for example, avian live vaccine and for the purpose of producing avian live vaccine, a suggested promising method is to insert exogenous DNA into Fowlpoxvirus in lieu of vaccinia virus (Avian Diseases, vol. 30, No. 1, 24–27). However, comparing vaccinia virus and Fowlpoxvirus, they belong to different genera; the former belonging to the genus Orthopoxvirus and the latter to the genus Avipoxvirus. Further, there is a difference in a length of genome by about 1.5 times because the former has a genome length of about 180 Kb and the latter has a genome length of 260 to 270 Kb. Furthermore, with vaccinia virus, its genome DNA structure has been clarified to a remarkable extent, but only restriction enzyme cleavage pattern of genome DNA is known with Fowlpoxvirus (J. Gen. Virol., 38, 135–147 (1977)); turning to function of genome DNA, the presence of thymidine kinase gene is merely proved [J. Gen. Virol., 67, 1591–1600 (1986)]. Accordingly, it is expected that application of the aforesaid method of constructing recombinant vaccinia virus to Avipoxvirus would be accompanied by many difficulties. In addition, it was quite unknown as to if the recombinant Avipoxvirus capable of proliferation in which exogenous DNA has been inserted into genome DNA might be successfully constructed.

SUMMARY OF THE INVENTION

As a result of extensive investigations on such a technical level, aiming at construction of the recombinant Avipoxvirus capable of proliferation in which exogenous DNA has been inserted into genome DNA, the present inventors have found that the recombinant Avipoxvirus capable of proliferation can be obtained by identifying a DNA region non-essential to proliferation of Avipoxvirus and inserting exogenous DNA into the region.

Thus, according to the present invention, the recombinant Avipoxvirus in which exogenous DNA has been inserted into the DNA region non-essential to proliferation of Avipoxvirus is provided as a first invention; as a second invention, a plasmid vector into which at least a part of the non-essential DNA region described above has been inserted is provided; and as a third invention, there is provided a method of producing the recombinant Avipoxvirus which comprises surveying and identifying the DNA region non-essential to proliferation of Avipoxvirus by technique of utilizing DNA encoding an enzyme, of which activity is readily detectable, or, DNA having no homology to either host or virus DNA and, inserting exogenous DNA utilizing such DNA as encodes an enzyme or has no homology to either host or virus DNA.

BRIEF DESCRIPTION OF THE DRAWINGS

FIGS. 1(1) to 1(3) show examples of DNA regions non-essential to proliferation of Avipoxvirus referred to in the present invention.

FIGS. 4(1) and 4(2) illustrate procedures for producing a first hybrid plasmid referred to in the present invention.

FIGS. 6(1) to 6(3) illustrate procedures for producing a third or sixth hybrid plasmid.

DETAILED DESCRIPTION OF PREFERRED EMBODIMENTS

Any virus is usable as the virus used to insert exogenous DNA in the present invention as far as it is classified into the genus Avipoxvirus but preferred are those capable of growing in cells of fowls such as chicken, turkey, duck, etc. Specific examples include Fowlpoxvirus such as ATCC VR-251, ATCC VR-250, ATCC VR-229, ATCC VR-249, ATCC VR-228, Nishigawara strain, Shisui strain, etc.; and those akin to Fowlpoxvirus and used to avian live vaccine strain such as NP strain (chick embryo habituated dovepoxvirus Nakano strain), etc.

Upon practice of the present invention, a first hybrid plasmid into which an optional DNA fragment of Avipoxvirus genome has been inserted and a second hybrid plasmid ligated with DNA encoding a readily detectable enzyme under control of a promoter (cf. FIG. 2) or a fifth hybrid plasmid into which a DNA fragment having no substantial homology to both of host cell genome DNA and Avipoxvirus genome DNA (hereafter sometimes referred to non-homologous DNA fragment) has been inserted (cf. FIG. 3) are firstly produced.

A first hybrid plasmid can be produced by inserting an optional DNA fragment obtained by cleavage of the Avipoxvirus genome described above with an appropriate restriction enzyme into plasmid in a conventional manner. The plasmid used herein may be any plasmid as long as it is capable of inserting the DNA fragment described above. Specific examples are pBR 322, pBR 325, pBR 327, pBR 328, pUC 7, pUC8, pUC 9, pUC 18, pUC 19, etc.

Figure 2:
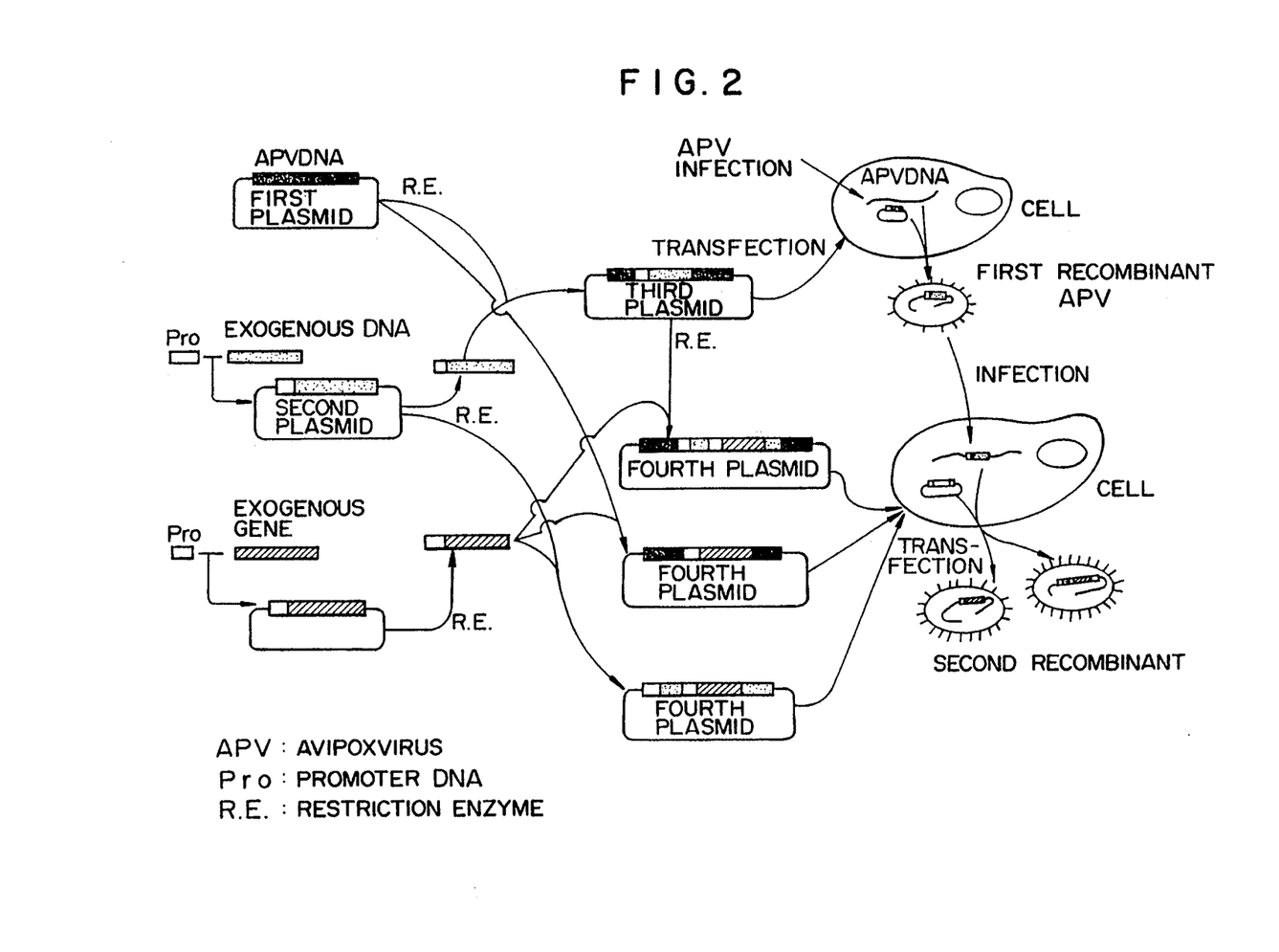
FIG. 2 indicates outline of the method for producing the recombinant which comprises surveying and identifying the DNA region non-essential to proliferation of Avipoxvirus and utilizing the region to make first or second recombinant Avipoxvirus.

A second hybrid plasmid shown in FIG. 2 can be produced by inserting DNA having a promoter function (sometimes simply referred to as a promoter) and DNA encoding an enzyme, of which activity is easily detectable, into a plasmid in a conventional manner.

The DNA having a promoter function as used in the present invention may be any DNA having any base sequence as long as it can effectively function as a promoter in the transcription system possessed by Avipoxvirus, irrespective of synthesized or naturally occurring DNA. Needless to say, promoters intrinsic to Avipoxvirus such as a promoter of Avipoxvirus gene coding for thymidine kinase are usable and, even DNA derived from virus other than Avipoxvirus or DNA derived from eukaryote or prokaryote can be naturally used in the present invention, as far as it meets the requirement described above. Concrete examples of these promoters include promoters of vaccinia virus illustrated in Journal of Virology, September 1984, 662–669, specifically, a promoter of vaccinia virus gene coding for 7.5K polypeptide, a promoter of vaccinia virus gene coding for 19K polypeptide, a promoter of vaccinia virus gene coding for 42K polypeptide, a promoter of vaccinia virus gene coding for thymidine kinase polypeptide, a promoter of vaccinia virus gene coding for 28K polypeptide, etc.

The DNA coding for an enzyme, of which activity is readily detectable, refers to DNA which produces enzyme protein in association with growth of recombinant virus when inserted with a suitable promoter into the genome region non-essential to proliferation of Avipoxvirus and of which activity is readily detectable, and refers to DNA coding for an enzyme which can be utilized for easy detection of recombinant virus depending upon detected enzyme activity and thus utilized for identification of the genome region non-essential to proliferation of Avipoxvirus. As specific examples of these enzymes, mention may be made of peroxidase, glucose oxidase, alkali phosphatase, glucose-6-phosphate dehydrogenase, $\beta$-galactosidase, etc. In these enzymes, enzyme activity can be sensitively detected by the addition of specific substrate.

Figure 3:
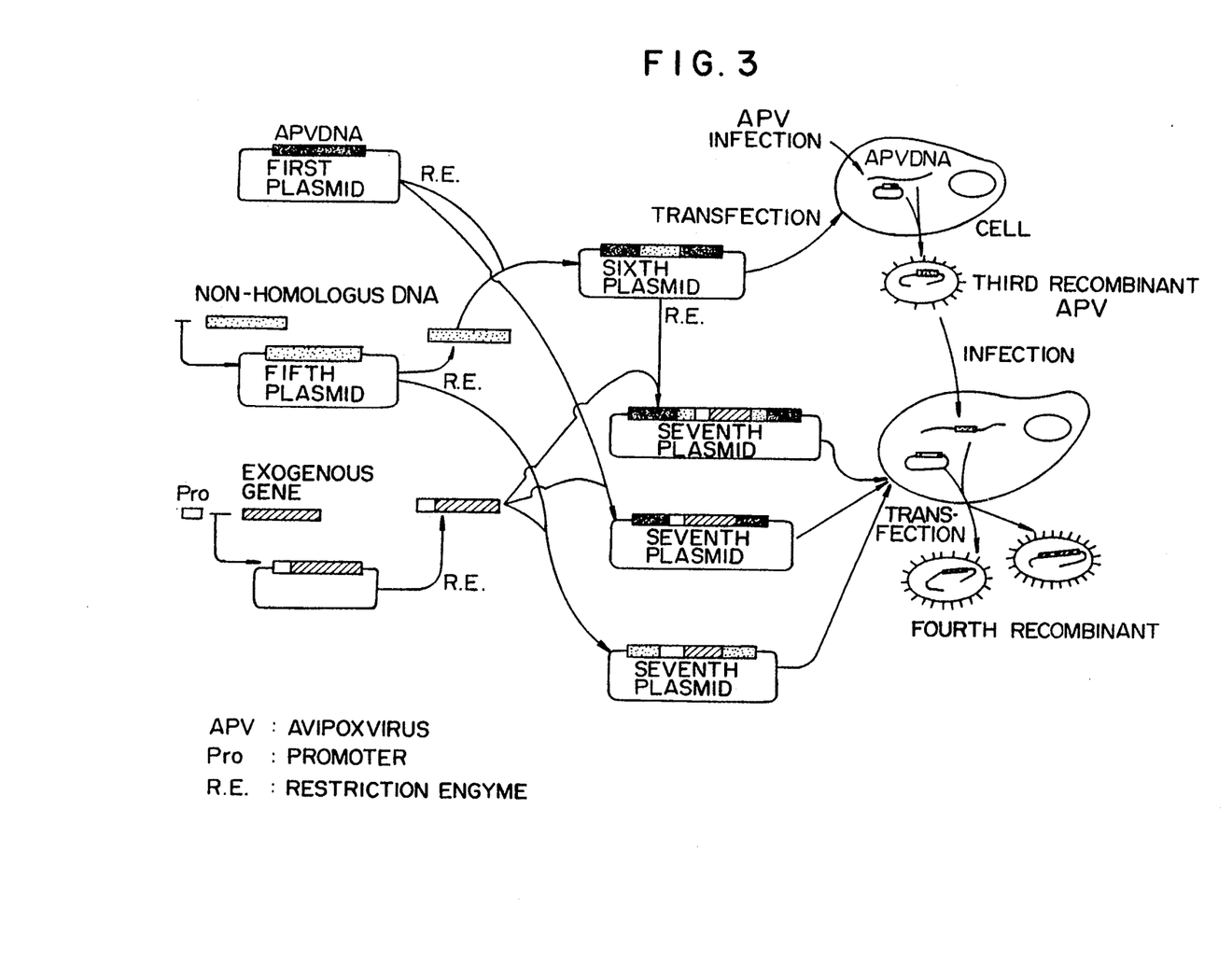
FIG. 3 indicates outline of the method for producing the recombinant which comprises surveying and identifying the DNA region non-essential to proliferation of Avipoxvirus and utilizing the region to make third or fourth recombinant Avipoxvirus.
Figure 4:
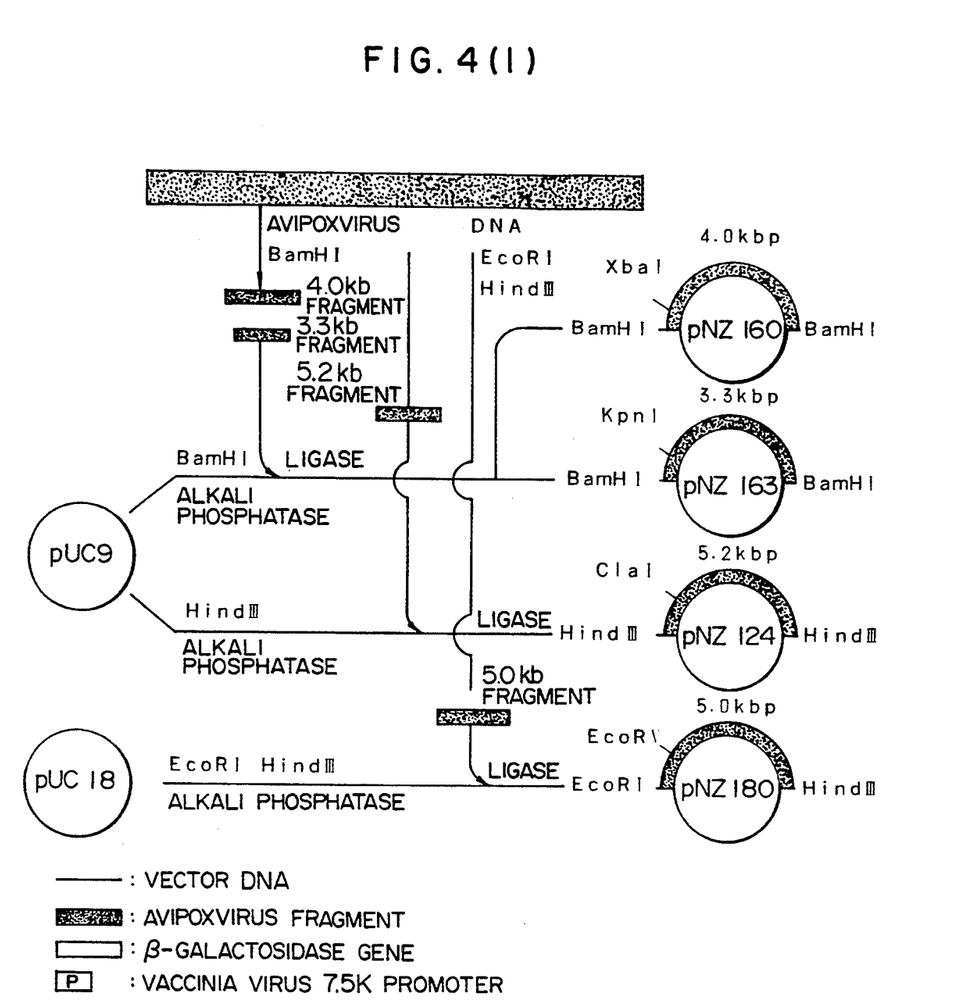

Further the fifth hybrid plasmid shown in FIG. 3 is produced by inserting a non-homologous DNA fragment having no substantial homology to any of host cell genome DNA and Avipoxvirus genome DNA into a plasmid in a conventional manner.

The non-homologous DNA fragment as used in the present invention refers to a DNA fragment, when hybridized with plaque of Avipoxvirus using as a probe the DNA fragment labeled with a radio isotope by means of the nick translation method, etc., that becomes negative in the measurement results of autoradiography.

Further the host cell as used in the present invention may be any cell as long as it is infectious with Avipoxvirus. Specific examples include chick-derived culture cells such as chick embryo fibroblasts (CEF), etc. As a matter of course, chick chorioallantoic membrane or the like is also included in the category of the host cell.

These plasmids used to produce a second hybrid plasmid or a fifth hybrid plasmid are not particularly limited and those as in a first hybrid plasmid can be used.

According to the present invention, next, a DNA fragment fully containing a promoter and DNA coding for the enzyme is produced from the second hybrid plasmid, or, the non-homologous DNA fragment described above from the fifth hybrid plasmid and, the DNA fragment is inserted into the virus DNA fragment of the first hybrid plasmid, whereby a third hybrid plasmid or sixth hybrid plasmid is obtained.

In the present invention, the third or sixth hybrid plasmid is transfected or transferred into host cell previously infected with Avipoxvirus thereby to confirm the presence or absence of the first or third recombinant Avipoxvirus formed. Transfection of plasmids into host cell may be performed in a conventional manner, for example, by the calcium phosphate method, the liposome method, the micro injection method, the electroporation method, etc.

Selection as to whether or not the first recombinant Avipoxvirus is constructed by a series of operations described above may be made in a conventional manner. For example, in the case of using $\beta$-galactosidase gene as DNA coding for enzyme, agarose medium containing chloropenolred-$\beta$-D-galactopyranoside (CPRG) is laid on medium for forming plaque of the recombinant Avipoxvirus in layers, after plaque has been recognized on the medium, followed by incubation at 37° C., where plaque stained in red may be selected.

Further in case that the sixth hybrid plasmid has been containing the non-homologous DNA fragment is transfected into Avipoxvirus-infected host cell, after plaque is recognized in medium for forming plaque of the recombinant Avipoxvirus, plaque hybridization is performed using the DNA as a probe and the third recombinant Avipoxvirus may be selected.

In case that the recombinant Avipoxvirus is thus obtained by detection of enzyme activity or detection of positive clone by plaque hybridization as a means of the selection, it is indicated that the DNA fragment derived from Avipoxvirus used for construction of the first hybrid plasmid is a DNA region non-essential to proliferation of Avipoxvirus.

In the present invention, a fourth or seventh hybrid plasmid is produced utilizing, as an insertion site, a ligation fragment of the promoter and DNA coding for readily detectable enzyme under its control in the second hybrid plasmid shown in FIG. 2 as an insertion site; alternatively, utilizing, as an insertion site, a ligation fragment of the non-homologous DNA fragment contained in the sixth hybrid plasmid shown in FIG. 3. This hybrid plasmid contains a promoter and exogenous DNA capable of expression under control of the promoter but does not contain the DNA coding for readily detectable enzyme described above or the non-homologous DNA fragment; or, even though they are contained, is divided by insertion of the promoter and exogenous DNA capable of expression under its control.

As methods for producing such fourth or seventh hybrid plasmid, mention may be made of, for example, the following methods.

(1) Method which comprises inserting a promoter and exogenous DNA capable of expression under its control into hybrid plasmid into which whole or a part of the fragments in the non-essential DNA region described above has/have been incorporated:

In this method, the aforesaid first hybrid plasmid can be utilized. As far as the non-essential DNA region is possessed wholly or partly, other hybrid plasmid independently produced may also be used.

(2) Method utilizing the DNA portion coding for readily detectable enzyme in the third hybrid plasmid described above (cf. FIGS. 1(1) to (3)) of non-homologous DNA portion in the fifth hybrid plasmid described above (cf. FIG. 3):

In this method, there are, for example, a technique that exogenous DNA or a promoter and exogenous DNA is/are inserted, respectively, in place of the DNA portion or the promoter and the DNA portion, a technique that a promoter and exogenous DNA capable of expression under its control are separately inserted into the DNA portion or the promoter portion.

(3) Method utilizing an insertion fragment of the second hybrid plasmid shown in FIG. 2 or the fifth hybrid plasmid shown in FIG. 3:

In this case, there is exemplified a technique that a promoter and exogenous DNA capable of expression under its control are separately inserted into the promoter portion, the DNA portion coding for readily detectable enzyme or the non-homologous DNA portion.

In the present invention, then, the fourth or seventh hybrid plasmid is transfected into host cell infected with the third or sixth recombinant Avipoxvirus in a conventional manner, whereby the objective second or fourth recombinant Avipoxvirus is produced. This operation may be carried out under conditions similar to those in the case of producing the first or third recombinant Avipoxvirus.

The activity of readily detectable enzyme has been lost in the second recombinant Avipoxvirus obtained. Therefore, the second recombinant Avipoxvirus can easily be isolated by selecting plaque showing no activity in the selection method of the first recombinant Avipoxvirus. The fourth recombinant Avipoxvirus obtained can easily be isolated by plaque hybridization using the aforesaid exogenous DNA or promoter or both of them as a probe(s), change in phenotype based on insertion of the exogenous DNA, immunoassay of protein formed by expression of the exogenous DNA, etc.

The present invention includes, as a matter of course, direct production of the objective recombinant Avipoxvirus which comprises omitting the step of previously surveying and identifying the DNA region non-essential to proliferation of Avipoxvirus but directly producing a plasmid having inserted a promoter and exogenous DNA into an optional DNA fragment derived from Avipoxvirus through isolation of the first or third recombinant Avipoxvirus, performing recombinant operation homologous to Avipoxvirus and obtaining the recombinant Avipoxvirus from the plaque obtained by plaque hybridization using the exogenous DNA or promoter or both of them as a probe(s), change in phenotype based on insertion of the exogenous DNA or immunoassay of protein formed by expression of the exogenous DNA.

Thus in the second or fourth recombinant Avipoxvirus obtained in accordance with the present invention, the exogenous DNA inserted is expressed and the objective polypeptide is produced in association with its growth. Accordingly, in the case of using Avipoxvirus provided in the present invention as attenuated vaccine and using DNA coding for antigens associated with prevention from infection or prevention from onset with pathogens of various infectious diseases (for example, Marek's disease, infectious laryngotracheobronchitis, infectious coryza, coccidioidosis, etc.), effective live vaccine against single or a plurality of infectious diseases can be provided.

Therefore, according to the present invention, the recombinant Avipoxvirus in which exogenous DNA has been inserted into the DNA region non-essential to proliferation of Avipoxvirus and a plasmid vector containing the DNA region non-essential to proliferation of Avipoxvirus which is useful for production of the recombinant Avipoxvirus can be obtained, respectively. Further, according to the present invention, an effective method for production of the recombinant Avipoxvirus utilizing the DNA region non-essential to proliferation of Avipoxvirus can be provided.

The present invention will be described in more detail with reference to the examples below.

EXAMPLE 1

Preparation of Avipoxvirus Genome DNA

Avipoxvirus NP strain (chick embryo habituated dovepoxvirus Nakano strain, manufactured by Japan Pharmacy Co., Ltd.) was inoculated on chick embryo fibroblasts cultured in a 75 $cm^2$ culture flask in 1 p.f.u./-cell. After culturing in an incubator at 37° C. in 5% $CO_2$ for 2 hours, 15 ml of Eagle's MEM medium supplemented with 10% Tryptose phosphate broth (Difco Co., Ltd.) and 0.03% L-glutamine was added followed by incubation in an incubator for 4 days at 37° C. in 5% $CO_2$. Then the culture supernatant was centrifuged at 3000 r.p.m. for 10 minutes to recover the supernatant. The supernatant was centrifuged at 25000 r.p.m. (about 98000×g) for an hour and the precipitates were recovered. The precipitates were suspended in a DNase reaction buffer (50 mM Tris, pH 7.5, 1 mM $MgCl_2$) of a 1/10 volume of the culture supernatant and DNase I (Boehringer Mannheim Co., Ltd.) was added to the suspension in 9 μg/ml followed by reacting at 37° C. for 30 minutes. After the reaction, 25 mM EDTA.2Na was added and the mixture was allowed to stand at room temperature for 30 minutes. Thereafter, 500 μg/ml of proteinase K (Boehringer Mannheim Co., Ltd.) and sodium dodecyl sulfate (SDS) were added to the mixture in a 1% concentration followed by reacting at 37° C. overnight. After gently treating with phenol-chloroform, the reaction mixture was precipitated with ethanol to give 0.5 μg of virus DNA.

EXAMPLE 2

Production of a First Hybrid Plasmid Containing Avipoxvirus Genome Fragment (cf. FIG. 5)

(1) Production of plasmid (pNZ 180) containing about 5.0 Kb EcoR I-Hind III fragment of DNA of Avipoxvirus NP strain:

After digesting 2 μg of pUC 18 (manufactured by Pharmacia Inc. with EcoRI and Hind III, extraction was performed with phenol-chloroform (1:1) to recover pUC 18 cleaved by precipitation with ethanol. 5'-End phosphate was removed by treating with alkali phosphatase. After extraction again with phenolchloroform, DNA was recovered by precipitation with ethanol. The cleaved pUC 18, 0.2 μg, and the digestion product of 1 μg of purified Avipoxvirus (NP strain) DNA with EcoR I and Hind III were ligated with each other. Competent *E. coli* JM 103 was transformed and cultured at 37° C. for 15 hours in LB agar medium supplemented with 0,003% of 5-bromo-4-chloro-3-indolyl-β-D-galactopyranoside, 0.03 mM of isopropyl-8-D-galactopyranoside and 40 μg/ml of ampicillin. White colony out of the transformed E. coli grown on agar medium was cultured at 37° C. for 15 hours in LB liquid medium added with 40 μg/ml of ampicillin and plasmid was extracted by the method of Birnboim and Doly [Nucleic Acid Research, 7, 1513 (1979)]. After digesting with EcoR I and Hind III, a hybrid plasmid having a fragment of the same length as that of the original Avipoxvirus DNA EcoR I-Hind III fragment was detected by 0.6% agarose electrophoresis, which was named pNZ 180. A restriction enzyme map of the about 5.0 Kb EcoR I-Hind III fragment is shown in FIG. 1(a). pNZ 180 is a first plasmid in the present invention.

(2) Production of plasmid (pNZ 160) containing about 4.0 Kb BamH I fragment of Avipoxvirus NP strain:

A hybrid plasmid was obtained in a manner similar to (1) except that vector pUC 18 used in (1) was changed to pUC 9 and about 4.0 Kb BamH I fragment of NP strain DNA was used in lieu of EcoR I-Hind III fragment. This hybrid plasmid was named pNZ 160. A restriction enzyme map of about 4.0 Kb BamH I fragment is shown in FIG. 1(*b*) and pNZ 160 is a first plasmid in the present invention.

(3) Production of plasmid (pNZ 163) containing about 3.3 Kb BamH I fragment of Avipoxvirus NP strain:

A hybrid plasmid was obtained in a manner similar to (1) except that vector pUC 18 used in (1) was changed to pUC 9 and about 3.3 Kb BamH I fragment of NP strain DNA was used in lieu of EcoR I-Hind III fragment. This hybrid plasmid was named pNZ 163. A restriction enzyme map of about 3.3 Kb BamH I fragment is shown in FIG. 1(*c*) and pNZ 163 is a first plasmid in the present invention.

(4) Production of plasmid (pNZ 124) containing about 5.2 Kb Hind III fragment of Avipoxvirus NP strain:

A hybrid plasmid was obtained in a manner similar to (1) except that vector pUC 18 used in (1) was changed to pUC 9 and about 5.2 Kb Hind III fragment of NP strain DNA was used in lieu of EcoR I-Hind III fragment. This hybrid plasmid was named pNZ 124. A restriction enzyme map of about 5.2 Kb Hind III fragment is shown in FIG. 1(*d*) and pNZ 124 is a first plasmid in the present invention.

(5) Production of plasmid (pNZ 131) containing about 7.3 Kb EcoR I fragment of Avipoxvirus NP strain:

A hybrid plasmid was obtained in a manner similar to (1) except that about 7.3 Kb EcoR I fragment of NP strain was used. This hybrid plasmid was named pNZ 131. A restriction enzyme map of about 7.3 Kb EcoR I fragment is shown in FIG. 1(*e*). pNZ 131 is a first plasmid in the present invention.

(6) Production of plasmid (pNZ 133) containing about 7.3 Kb EcoR I fragment of Avipoxvirus NP strain:

A hybrid plasmid was obtained in a manner similar to (1) except that about 7.3 Kb EcoR I fragment of NP strain was used. This hybrid plasmid was named pNZ 133. A restriction enzyme map of about 7.3 Kb EcoR I fragment is shown in FIG. 1(*f*). pNZ 133 is a first plasmid in the present invention.

(7) Production of plasmid (pNZ 134) containing about 6.5 Kb EcoR I fragment of Avipoxvirus NP strain:

A hybrid plasmid was obtained in a manner similar to (1) except that about 6.5 Kb EcoR I fragment of NP strain was used. This hybrid plasmid was named pNZ 134. A restriction enzyme map of about 6.5 Kb EcoR I fragment is shown in FIG. 1(*g*). pNZ 134 is a first plasmid in the present invention.

(8) Production of plasmid (pNZ 135) containing about 8.5 Kb EcoR I fragment of Avipoxvirus NP strain:

A hybrid plasmid was obtained in a manner similar to (1) except that about 8.5 Kb EcoR I fragment of NP strain was used. This hybrid plasmid was named pNZ 135. A restriction enzyme map of about 8.5 Kb EcoR I fragment is shown in FIG. 1(*h*). pNZ 135 is a first plasmid in the present invention.

(9) Production of plasmid (pNZ 137) containing about 6.6 Kb EcoR I fragment of Avipoxvirus NP strain:

A hybrid plasmid was obtained in a manner similar to (1) except that about 6.6 Kb EcoR I fragment of NP strain was used. This hybrid plasmid was named pNZ 137. A restriction enzyme map of about 6.6 Kb EcoR I fragment is shown in FIG. 1(*i*). pNZ 137 is a first plasmid in the present invention.

(10) Production of plasmid (pNZ 142) containing about 4.1 Kb EcoR I fragment of Avipoxvirus NP strain:

A hybrid plasmid was obtained in a manner similar to (1) except that about 7.3 Kb EcoR I fragment of NP strain was used. This hybrid plasmid was named pNZ 142. A restriction enzyme map of about 4.1 Kb EcoR I fragment is shown in FIG. 1(*j*). pNZ 142 is a first plasmid in the present invention.

(11) Production of plasmid (pNZ 144) containing about 5.5 Kb EcoR I fragment of Avipoxvirus NP strain:

A hybrid plasmid was obtained in a manner similar to (1) except that about 5.5 Kb EcoR I fragment of NP strain was used. This hybrid plasmid was named pNZ 144. A restriction enzyme map of about 5.5 Kb EcoR I fragment is shown in FIG. 1(*k*). pNZ 144 is a first plasmid in the present invention.

(12) Production of plasmid (pNZ 145) containing about 4.9 Kb EcoR I fragment of Avipoxvirus NP strain:

A hybrid plasmid was obtained in a manner similar to (1) except that about 4.9 Kb EcoR I fragment of NP strain was used. This hybrid plasmid was named pNZ 145. A restriction enzyme map of about 4.9 Kb EcoR I fragment is shown in FIG. 1(*l*). pNZ 145 is a first plasmid in the present invention.

(13) Production of plasmid (pNZ 147) containing about 5.8 Kb EcoR I fragment of Avipoxvirus NP strain:

A hybrid plasmid was obtained in a manner similar to (1) except that about 5.8 Kb EcoR I fragment of NP strain was used. This hybrid plasmid was named pNZ 147. A restriction enzyme map of about 5.8 Kb EcoR I fragment is shown in FIG. 1(*m*). pNZ 147 is a first plasmid in the present invention.

EXAMPLE 3

Production of the Second Hybrid Plasmid (pNZ 76) Ligated with a Promoter and DNA Coding for Readily Detectable Enzyme under its Control (cf. FIG. 5)

(1) Production of plasmid (pUWP-1) containing a promoter of gene coding for vaccinia virus 7.5K dalton peptide:

A plasmid having inserted about 0.26 kbp of Sal I-Rsa I fragment containing a promoter of DNA coding for 7.5K dalton peptide of vaccinia virus WR strain [Cell, 125, 805–813 (1981)] into Sal I-Sma I portion of pUC 9 was named pUWP-1.

Figure 5:
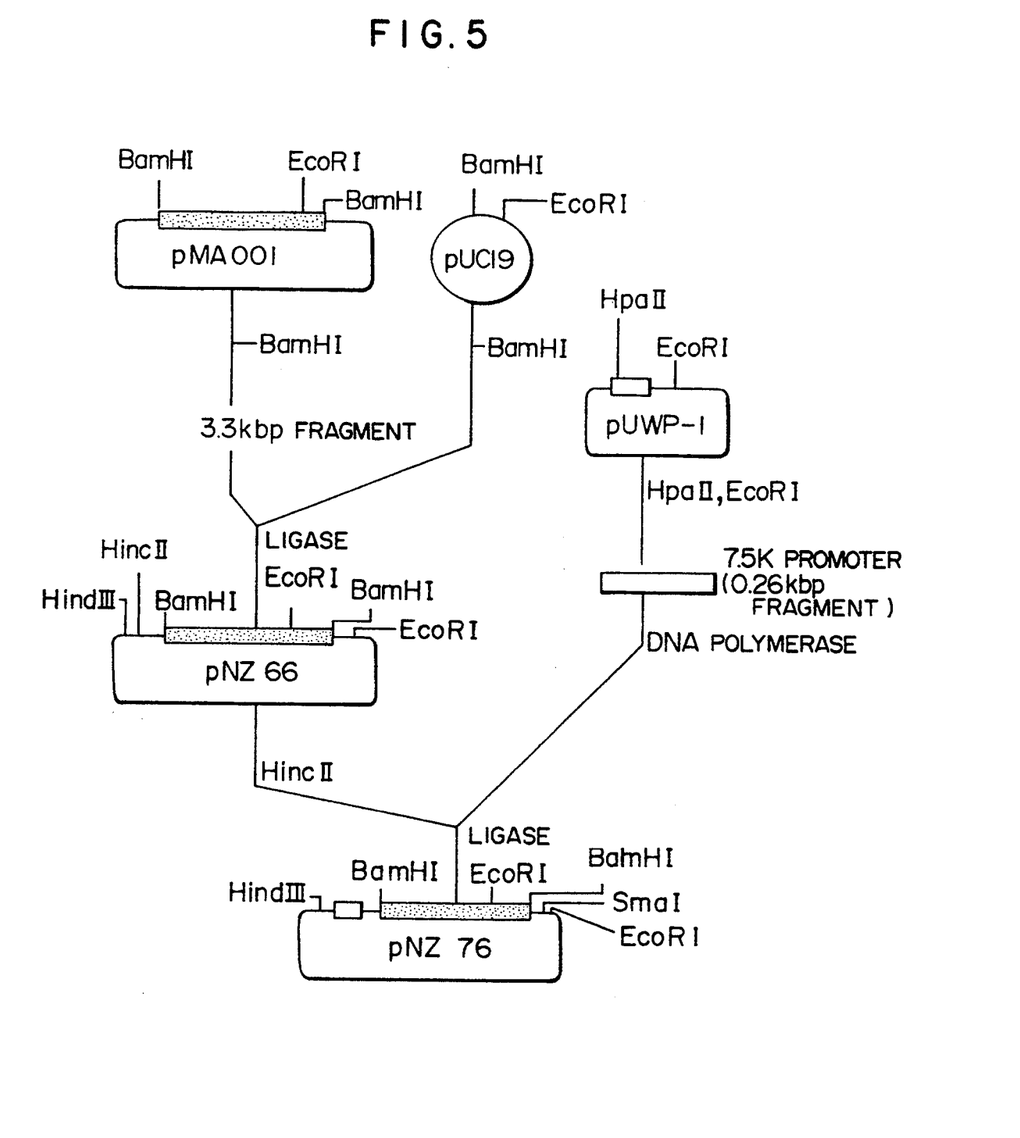
FIG. 5 illustrates procedures for producing a second or fifth hybrid plasmid.
Figure 6:
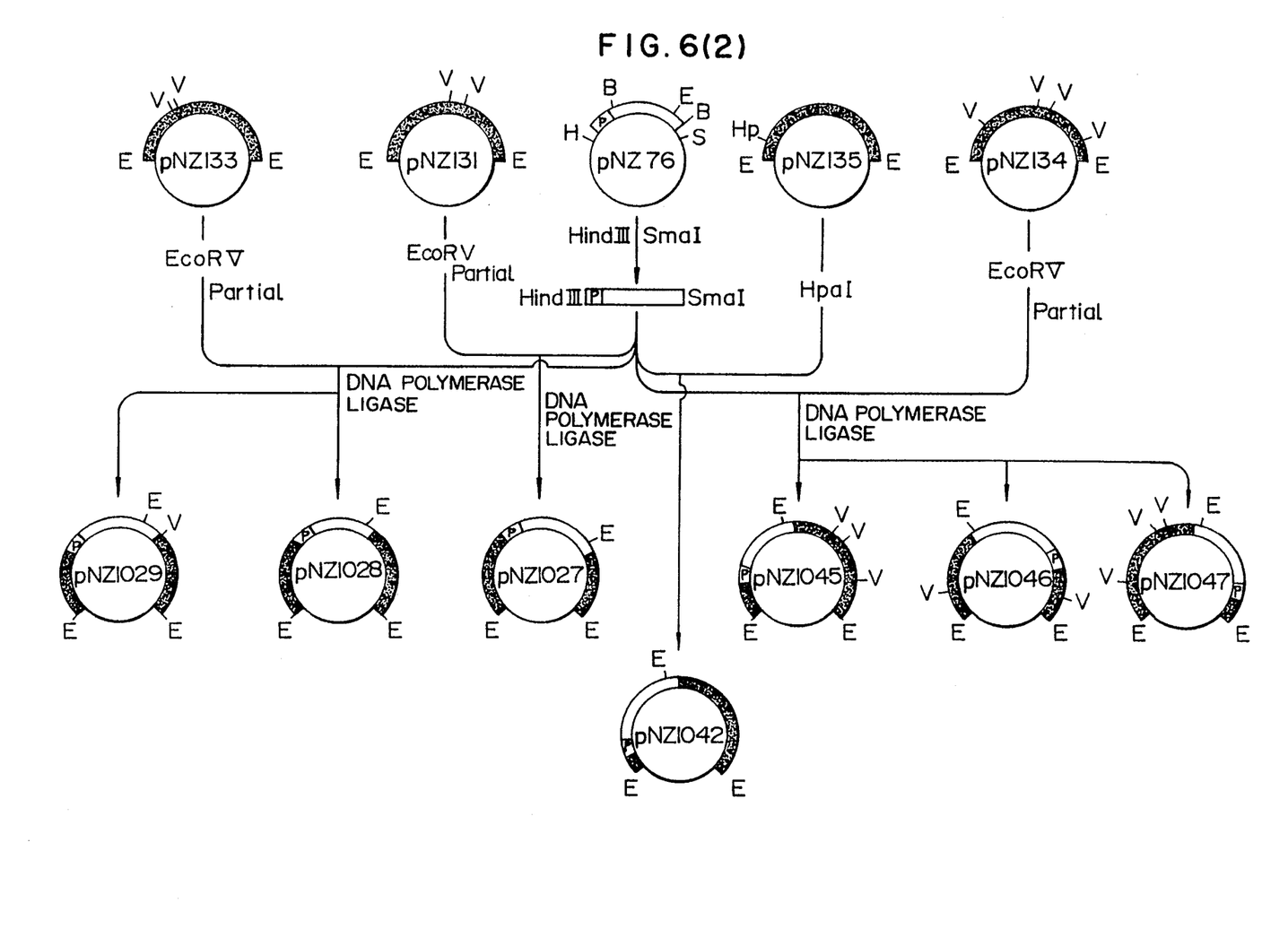
Figure 6I:
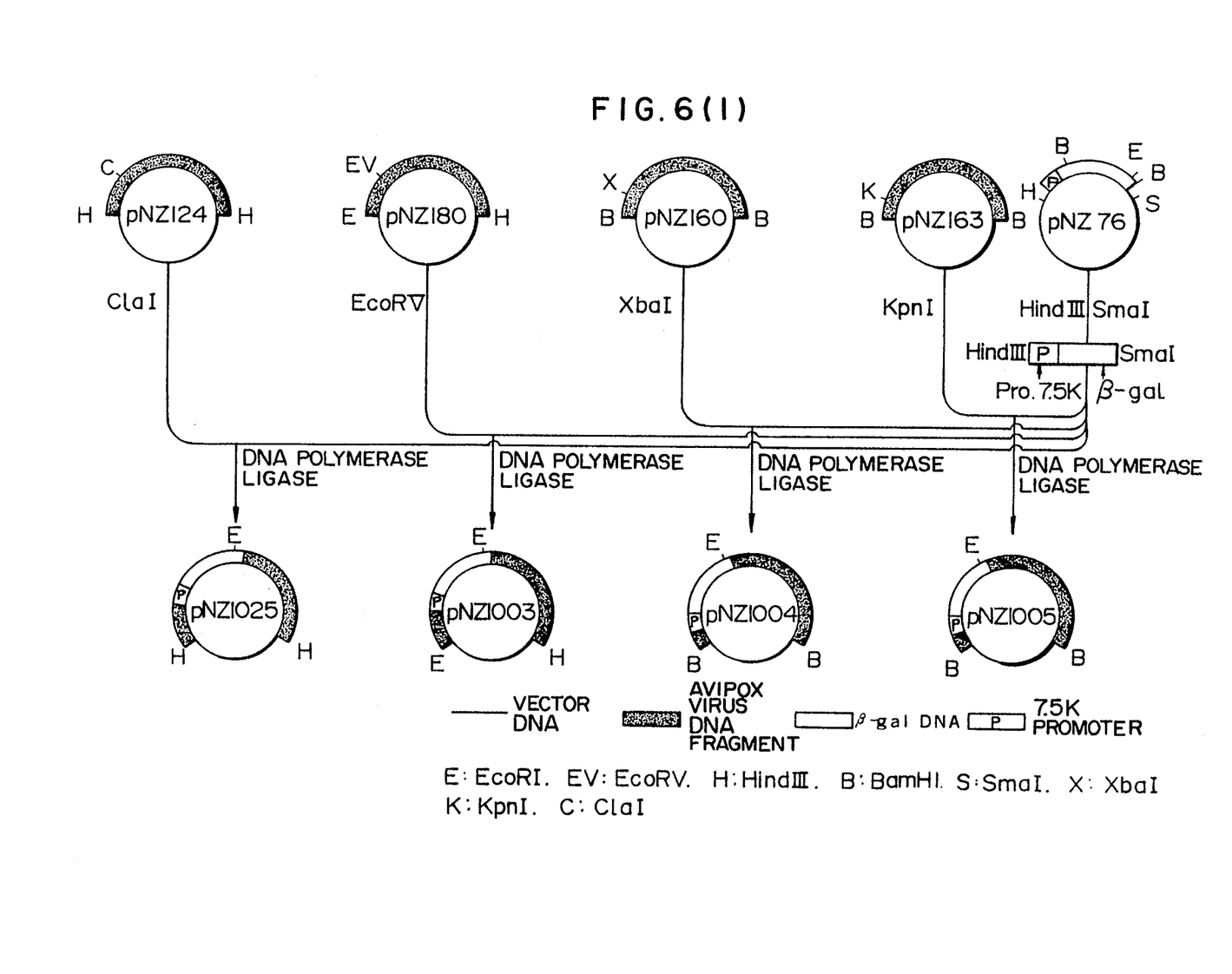

(2) Production of plasmid (pNZ 76) having ligated β-galactosidase gene with 7.5K promoter (cf. FIG. 5)

After digesting 10 μg of pMA 001 [Shirakawa et al., Gene, 28, 127 (1984)] with BamH I, β-galactosidase gene (about 3.3 kbp) was recovered in a manner similar to Example 1 (1). On the other hand, after digesting 0.3 μg of pUC 19 with BamH I, extraction was performed with phenol-chloroform and recovery was made through precipitation with ethanol. By ligation with the β-galactosidase gene prepared as described above, hybrid plasmid pNZ 66 was produced.

On the other hand, 40 μg of pUWP-1 was digested with Hpa II and EcoR I and, a fragment of about 0.26 kbp containing 7.5K promoter was separated by 1.5% low melting point agarose electrophoresis (70 volts, 6 hours) and DNA was recovered by operation similar to Example 2 (1). The cohesive end of this DNA fragment was made the blunt end by DNA polymerase. After 0.3 μg of pNZ 66 was digested with Hinc II, extraction was performed with phenol-chloroform and recovery was made through precipitation with ethanol. By ligation with about 0.26 kbp of the 7.5K promoter gene described above, a hybrid plasmid was obtained and named pNZ 76. pNZ 76 corresponds to a second hybrid plasmid in the present invention.

The 7.5K promoter and β-galactosidase gene do not show homology to host cell genome DNA and Avipoxvirus DNA and is thus usable also as a fifth plasmid, as a matter of course.

EXAMPLE 4

Production of Third Hybrid Plasmid from the First Hybrid Plasmid and the Second Hybrid Plasmid (cf. FIG. 6)

(1) Production of hybrid plasmid (pNZ 1003) having inserted a ligation fragment of vaccinia virus 7.5K promoter and β-galactosidase DNA into EcoR V site of pNZ 180

After digesting 10 μg of pNZ 76 with Hind III and Sma I, a fragment of about 3.6 kbp was separated by 0.7% low melting point agarose electrophoresis (40 volts, 20 hours). After the DNA fragment was confirmed by staining with ethidium bromide, gel was excised, treated with phenol and precipitated with ethanol to recover the DNA fragment.

On the other hand, 1 μg of pNZ 180 was digested with EcoR V, extracted with phenol-chloroform and precipitated with ethanol to recover the same. The cleaved pNZ 180 DNA, 0.3 μg, was mixed with about 0.4 μg of the aforesaid about 3.6 kbp fragment (ligation fragment of 7.5K promoter DNA and β-galactosidase gene) and the cohesive end was made the blunt end by DNA polymerase. After extracting with phenol-chloroform, the DNA was recovered. The recovered DNA was ligated with ligase. Competent E. coli JM 103 strain was transformed and allowed to grow at 37° C. for 15 hours in LB agar medium supplemented with 40 μg/ml of ampicillin. A plasmid was recovered from E. coli grown in a manner similar to Example 2 (1) and digested with BamH I. A hybrid plasmid containing a β-galactosidase gene fragment (about 3.3 kbp) was selected by 0.5% agarose electrophoresis, which was named pNZ 1003.

(2) Production of hybrid plasmid (pNZ 1004) having inserted a ligation fragment of vaccinia virus 7.5K promoter and β-galactosidase DNA into Xba I site of pNZ 160

A hybrid plasmid containing a β-galactosidase gene fragment (about 3.3 kbp) was selected in a manner similar to (1) except that pNZ 180 and restriction enzyme EcoR V used in (1) were changed to pNZ 160 and Xba I, respectively. This hybrid plasmid was named pNZ 1004.

(3) Production of hybrid plasmid (pNZ 1005) having inserted a ligation fragment of vaccinia virus 7.5K promoter and β-galactosidase DNA into Kpn I site of pNZ 163

A hybrid plasmid containing a β-galactosidase gene fragment (about 3.3 kbp) was selected in a manner similar to (1) except that pNZ 180 and restriction enzyme EcoR V used in (1) were changed to pNZ 163 and Kpn I, respectively. This hybrid plasmid was named pNZ 1005.

(4) Production of hybrid plasmid (pNZ 1025) having inserted a ligation fragment of vaccinia virus 7.5K promoter and β-galactosidase DNA into Cla I site of pNZ 124

A hybrid plasmid containing a β-galactosidase gene fragment (about 3.3 kbp) was selected in a manner similar to (1) except that pNZ 180 and restriction enzyme EcoR V used in (1) were changed to pNZ 124 and Cla I, respectively. This hybrid plasmid was named pNZ 1025.

(5) Production of hybrid plasmid (pNZ 1027) having inserted a ligation fragment of vaccinia virus 7.5K promoter and β-galactosidase DNA into EcoR V site of pNZ 131

A hybrid plasmid containing a β-galactosidase gene fragment (about 3.3 kbp) was selected in a manner similar to (1) except that pNZ 180 used in (1) was changed to pNZ 131 and partially digested with restriction enzyme EcoR V. This hybrid plasmid was named pNZ 1027.

(6) Production of hybrid plasmids (pNZ 1028, pNZ 1029) having inserted a ligation fragment of vaccinia virus 7.5K promoter and β-galactosidase DNA into EcoR V site of pNZ 133

Hybrid plasmids containing a β-galactosidase gene fragment (about 3.3 kbp) were selected in a manner similar to (1) except that pNZ 180 used in (1) was changed to pNZ 133 and partially digested with restriction enzyme EcoR V. These hybrid plasmids were named pNZ 1028 and pNZ 1029. pNZ 1028 and pNZ 1029 were determined by analysis of cleavage pattern with restriction enzymes BamH I and EcoR V.

(7) Production of hybrid plasmids (pNZ 1045, pNZ 1046, pNZ 1047) having inserted a ligation fragment of vaccinia virus 7.5K promoter and β-galactosidase DNA into EcoR V site of pNZ 134

A hybrid plasmid containing a β-galactosidase gene fragment (about 3.3 kbp) was selected in a manner similar to (1) except that pNZ 180 used in (1) was changed to PNZ 134 and partially digested with restriction enzyme EcoR V. These hybrid plasmids were named pNZ 1045, pNZ 1046 and pNZ 1047. pNZ 1045, pNZ 1046 and pNZ 1047 were determined by analysis of cleavage pattern with restriction enzymes BamH I and EcoR V, in a manner similar to (6).

(8) Production of hybrid plasmid (pNZ 1042) having inserted a ligation fragment of vaccinia virus 7.5K promoter and β-galactosidase DNA into Hpa I site of pNZ 135

A hybrid plasmid containing a β-galactosidase gene fragment (about 3.3 kbp) was selected in a manner similar to (1) except that pNZ 180 and restriction enzyme EcoR V used in (1) were changed to pNZ 135 and Hpa I, respectively. This hybrid plasmid was named pNZ 1042.

(9) Production of hybrid plasmid (pNZ 1030) having inserted a ligation fragment of vaccinia virus 7.5K promoter and β-galactosidase DNA into EcoR V site of pNZ 137

A hybrid plasmid containing a β-galactosidase gene fragment (about 3.3 kbp) was selected in a manner similar to (1) except that pNZ 180 used in (1) was changed to pNZ 137. This hybrid plasmid was named pNZ 1030.

(10) Production of hybrid plasmid (pNZ 1035) having inserted a ligation fragment of vaccinia virus 7.5K promoter and β-galactosidase DNA into Cla I site of pNZ 142

A hybrid plasmid containing a β-galactosidase gene fragment (about 3.3 kbp) was selected in a manner similar to (1) except that pNZ 180 and restriction enzyme EcoR V used in (1) were changed to pNZ 142 and Cla I, respectively. This hybrid plasmid was named pNZ 1035.

(11) Production of hybrid plasmids (pNZ 1040, pNZ 1041) having inserted a ligation fragment of vaccinia virus 7.5K promoter and β-galactosidase DNA into EcoR V site of pNZ 144

A hybrid plasmid containing a β-galactosidase gene fragment (about 3.3 kbp) was selected in a manner similar to (1) except that pNZ 180 used in (1) were changed to pNZ 144 and partially digested with restriction enzyme EcoR V. These hybrid plasmids were named pNZ 1040 and pNZ 1041, respectively. pNZ 1040 and pNZ 1041 were determined by analysis of cleavage pattern with restriction enzymes BamH I and EcoR V.

(12) Production of hybrid plasmids (pNZ 1031, pNZ 1032) having inserted a ligation fragment of vaccinia virus 7.5K promoter and β-galactosidase DNA into EcoR V site of pNZ 145

A hybrid plasmid containing a β-galactosidase gene fragment (about 3.3 kbp) was selected in a manner similar to (1) except that pNZ 180 used in (1) was changed to pNZ 145 and partially digested with restriction enzyme EcoR V. These hybrid plasmids were named pNZ 1031 and pNZ 1032. pNZ 1031 and pNZ 1032 were determined by analysis of cleavage pattern with restriction enzymes BamH I and EcoR V.

(13) Production of hybrid plasmid (pNZ 1033) having inserted a ligation fragment of vaccinia virus 7.5K promoter and β-galactosidase DNA into EcoR V site of pNZ 147

A hybrid plasmid containing a β-galactosidase gene fragment (about 3.3 kbp) was selected in a manner similar to (1) except that pNZ 180 used in (1) was changed to pNZ 145 and partially digested with restriction enzyme EcoR V. This hybrid plasmid was named pNZ 1033.

The 7.5K promoter and β-galactosidase gene contained in these plasmids do not show homology to host cell genome DNA and Avipoxvirus DNA and can thus be utilized as a sixth hybrid plasmid, as a matter of course.

EXAMPLE 5

Production of the Recombinant Avipoxvirus (1) Production of the recombinant Avipoxvirus by the DNA-calcium phosphate coprecipitation method Avipoxvirus NP strain was inoculated on chick embryo fibroblasts cultured in a 25 $cm^2$ culture flask in 0.05 p.f.u./cell. The hybrid plasmid, 50 μg, obtained in Example 4 was dissolved in 2.2 ml of sterilized water and, 2.5 ml of a mixture of 1% HEPES (GIBCO Co., Ltd.) and 0.6% sodium chloride and 50 μl of buffer solution obtained by mixing 70 mM disodium hydrogenphosphate 12 hydrate and 70 mM disodium hydrogenphosphate 2 hydrate in an equimolar amount were mixed with the solution to prepare an aqueous solution. The aqueous solution was transferred to a 15 ml tube (manufactured by Falcon Co., Ltd.) and 300 μl of 2M calcium chloride aqueous solution was dropwise added thereto while agitating with a stirrer to form DNA-calcium phosphate coprecipitates. Fourty five minutes after the inoculation of virus, 0.5 ml of the coprecipitates were dropwise added to the infected chick embryo fibroblasts. After settling in an incubator at 37° C. in 5% $CO_2$ for 30 minutes, 4.5 ml of Eagle's MEM medium supplemented with 5% bovine fetal serum, 0.03% L-glutamine and 10% Tryptose phosphate broth was added thereto. Three hours after, the culture supernatant was exchanged and cultured in an incubator for 3 days at 37° C. in 5% $CO_2$. The system including culture cells was frozen and thawed 3 times to give a solution of virus containing recombinant.

(2) Production of the recombinant Avipoxvirus by electroporation

Avipoxvirus NP strain was inoculated on chick embryo fibroblasts cultured in a 75 $cm^2$ culture flask in 0.05 p.f.u./cell. After culturing in an incubator at 37° C. in 5% $CO_2$ for 2 hours, 15 ml of Eagle's MEM medium supplemented with 5% bovine fetal serum, 0.03% L-glutamine and 10% Tryptose phosphate broth was added followed by incubation in an incubator at 37° C. in 5% $CO_2$ for further 2 hours. Infected cells were scrapped off with 0.05% trypsin (trypsin 1:250, Difco Co., Ltd.), washed twice with 10 ml of Saline G (0.8% NaCl, 0.04% KCl, 0.0395% $Na_2HPO_4.12H_2O$, 0.02% $KH_2PO_4$, 0.01% $MgCl_2.6H_2O$, 0.01% $CaCl_2$, 0.1% glucose, pH 7.1) and then 800 μl of Saline G (same as above). The hybrid plasmid, 10 μg, obtained in Example 4 was dissolved in 100 μl of Saline G and the solution was added to the infected cell suspension. After the mixture was thoroughly suspended, the suspension was transferred to a cuvette (Biorad Co., Ltd., for use in genepulser). Using the cell electroporation system (Biorad Co., Ltd., for use in genepulser), DNA was introduced under reaction conditions of 6 kv/cm and 0.1 msec (3 μFD) or 3 kv/cm and 0.4 msec (25 μFD). After the reaction, the system was settled for 10 minutes and then charged in a 25 $cm^2$ culture flask in which 5 ml of phenolred-free Eagle's MEM medium containing 5% bovine fetal serum, 10% Tryptose phosphate broth and 0.03% L-glutamine (Nissui ②) had been previously charged, followed by incubation in an incubator for 3 days in 5% $CO_2$. The system including culture cells was frozen and thawed 3 times to give a solution of virus containing recombinant.

EXAMPLE 6

Selection of the Recombinant by Chlorophenolred-$\beta$-galactopyranoside

The virus solution obtained in Example 5 was inoculated on chick embryo fibroblasts cultured in a 10 cm Petri dish. Two hours after, 10 ml of phenolred-free Eagle's MEM medium supplemented with 0.8% Bacto agar (manufactured by Difco Co., Ltd.), 5% bovine fetal serum, 0.03% L-glutamine and 10% Tryptose phosphate broth was put thereon in layers followed by incubation in an incubator at 37° C. in 5% $CO_2$ for 3 days. On the medium was put 10 ml of phenolred-free Eagle's MEM medium supplemented with 0.8% Bacto agar, 0.03% L-glutamine, 10% Tryptose phosphate broth and 0.03% chlorophenolred-$\beta$-D-galactopyranoside (Boehringer Mannheim) in layers followed by incubation in an incubator at 37° C. in 5% CO for 6 hours. Recombinant virus expresses $\beta$-galactosidase and changes chlorophenolred-$\beta$-galactopyranoside to red so that both agar and cells around the recombinant plaque became red and could be easily distinguished over non-recombinant. The recombinant formed from this red plaque was isolated with a sterilized Pasteur pippette. Each recombinant was named as shown in Table 1.

TABLE 1

| Parent Strain | Third Hybrid Plasmid | Recombinant |
|---|---|---|
| Avipoxvirus NP strain | pNZ 1003 | fNZ 1003 |
| " | pNZ 1004 | fNZ 1004 |
| " | pNZ 1005 | fNZ 1005 |
| " | pNZ 1025 | fNZ 1025 |
| " | pNZ 1027 | fNZ 1027 |
| " | pNZ 1028 | fNZ 1028 |
| " | pNZ 1029 | fNZ 1029 |
| " | pNZ 1045 | fNZ 1045 |
| " | pNZ 1046 | fNZ 1046 |
| " | pNZ 1047 | fNZ 1047 |
| " | pNZ 1042 | fNZ 1042 |
| " | pNZ 1030 | fNZ 1030 |
| " | pNZ 1035 | fNZ 1035 |
| " | pNZ 1040 | fNZ 1040 |
| " | pNZ 1050 | fNZ 1050 |
| " | pNZ 1031 | fNZ 1031 |
| " | pNZ 1032 | fNZ 1032 |
| " | pNZ 1033 | fNZ 1033 |

EXAMPLE 7

Selection of the Recombinant by Plaque Hybridization

The virus solution obtained in Example 5 was inoculated on chick embryo fibroblasts cultured in a 10 cm Petri dish. Two hours after, 10 ml of Eagle's MEM medium supplemented with 0.8% Bacto agar, 5% bovine fetal serum, 0.03% L-glutamine and 10% Tryptose phosphate broth was put thereon in layers followed by incubation in an incubator at 37° C. in 5% $CO_2$ for 3 days. On the medium was further put 10 ml of Eagle's MEM medium having the same composition as described above in layers followed by incubation in an incubator at 37° C. in 5% $CO_2$ for 3 days. Further, 10 ml of Eagle's MEM medium supplemented with 0.8% Bacto agar, 0.03% L-glutamine and 10% Tryptose phosphate broth and 0.01% of neutral red was put thereon in layers followed by incubation in an incubator at 37° C. in 5% CO for 12 hours to stain infected cells.

The agar medium was withdrawn from the Petri dish and a sterilized nylon membrane was pushed onto the surface of cells kept at 4° C. and remained on the bottom of the Petri dish to transfer the viruses thereon. After repeating a treatment with 0.5N NaOH for 10 minutes and 1M Tris-hydrochloride buffer for 5 minutes 3 times, the membrane was treated with 0.5M Tris-hydrochloride buffer for 5 minutes. The membrane was saturated with 2-fold SSC. (1-fold SSC, 0.15M NaCl, 0.015M $C_3H_4(OH)(COONa)_3$) and baked at 80° C. for 2 hours. The membrane was treated with 4-fold SET (0.6M NaCl, 0.08M Tris HCl, 4 mM EDTA, pH 7.8)-10-fold Denhardt-0.1% SDS at 68° C. for 2 hours. After adding 4×SET-10× Denhardt-0.1% SDS-modified salmon sperm DNA and a DNA coding for $\beta$-galactosidase labeled with $^{32}P$ by nick translation. The hybridization was carried out at 68° C. for 14 hours. After washing, the nylon membrane was contacted with an X-ray film and maintained at 4° C. Plaques thereby identified by autoradiography as containing the $\beta$-galactosidase gene were replated using a sterilized Pasteur pipette. The frequency of positive recombinants was about 0.02%.

EXAMPLE 8

Purification of the Recombinant Avipoxvirus

The red plaque isolated in Example 6 was suspended in 1 ml of Eagle's MEM and 200 $\mu$l of the suspension was inoculated on chick embryo fibroblasts cultured in a 10 cm Petri dish. Two hours after, 10 ml of phenolred-free Eagle's MEM medium supplemented with 0.8% Bacto agar, 5% bovine fetal serum, 0.03% L-glutamine and 10% Tryptose phosphate broth was laid thereon in layers followed by incubation in an incubator at 37° C. in 5% $CO_2$ for 3 days. On the medium was laid 10 ml of phenolred-free Eagle's MEM medium having the same composition described above in layers followed by incubation in an incubator at 37° C. in 5% $CO_2$ for 3 days. On the medium was laid 10 ml of phenolred-free Eagle's MEM medium supplemented with 0.8% Bacto agar, 0.03% L-glutamine, 10% Tryptose phosphate broth and 0.03% chlorophenol-red-$\beta$-D-galactopyranoside followed by incubation in an incubator at 37° C. in 5% $CO_2$ for 6 hours. The recombinant plaque was colored to red as in Example 6.

The foregoing operations were repeated in a similar manner to again purify the recombinant.

As the result, 3 recombinant plaques (red plaque) (0.04%) appeared with pNZ 1003, per 10 Petri dishes of 10 cm in which approximately 700 plaques appeared in Example 6; in the first plaque purification, 240 (26%) of the recombinant plaques appeared in 3 Petri dishes in which about 300 plaques appeared. In the second plaque purification, almost all plaques were recombinants. In other 18 recombinant viruses, similar results were obtained.

EXAMPLE 9

Analysis of the Genome DNA of the Recombinant Avipoxviruses

Each Avipoxvirus NP strain obtained in Example 8 was inoculated on chick embryo fibroblasts cultured in a 10 cm Petri dish in 1 p.f.u./cell. Virus DNA was isolated in a manner similar to Example 1. After 2 $\mu$g of each recombinant virus DNA was digested with BamH I or Hind III, fragments were separated by 0.5% agarose electrophoresis (25 V, 20 hours). After the DNA was transferred to a nylon membrane by the Southern's method [Journal of Molecular Biology, 98,503 (1975)], the DNA was immobilized onto the nylon membrane at 80° C. under reduced pressure. After treating with 4-fold SET-[0.6M NaCl, 0.08M Tris HCl (pH 7.8), 4 mM EDTA]-10-fold Denhardt-0.1% SDS at 68° C. for 2 hours, β-galactosidase gene DNA labeled with 32p by nick translation was hybridized with 4-fold SET-10-fold Denhardt-0.1% SDS-modified salmon sperm DNA at 68° C. for 14 hours. After washing and drying, a nylon membrane was put on an X ray film to perform autoradiography, whereby the presence of bands was confirmed. It was confirmed that these recombinant viruses contained the β-galactosidase genes in definite locations.

From these results, the DNA fragment ligated with promoter DNA and β-galactosidase gene is effective for selection of recombinant Avipoxvirus utilizing enzyme activity based on the readily detectable enzyme and also effective for selection of recombinant Avipoxvirus utilizing DNA having no substantial homology to host cell genome DNA and Avipoxvirus genome DNA.

Figure 1:
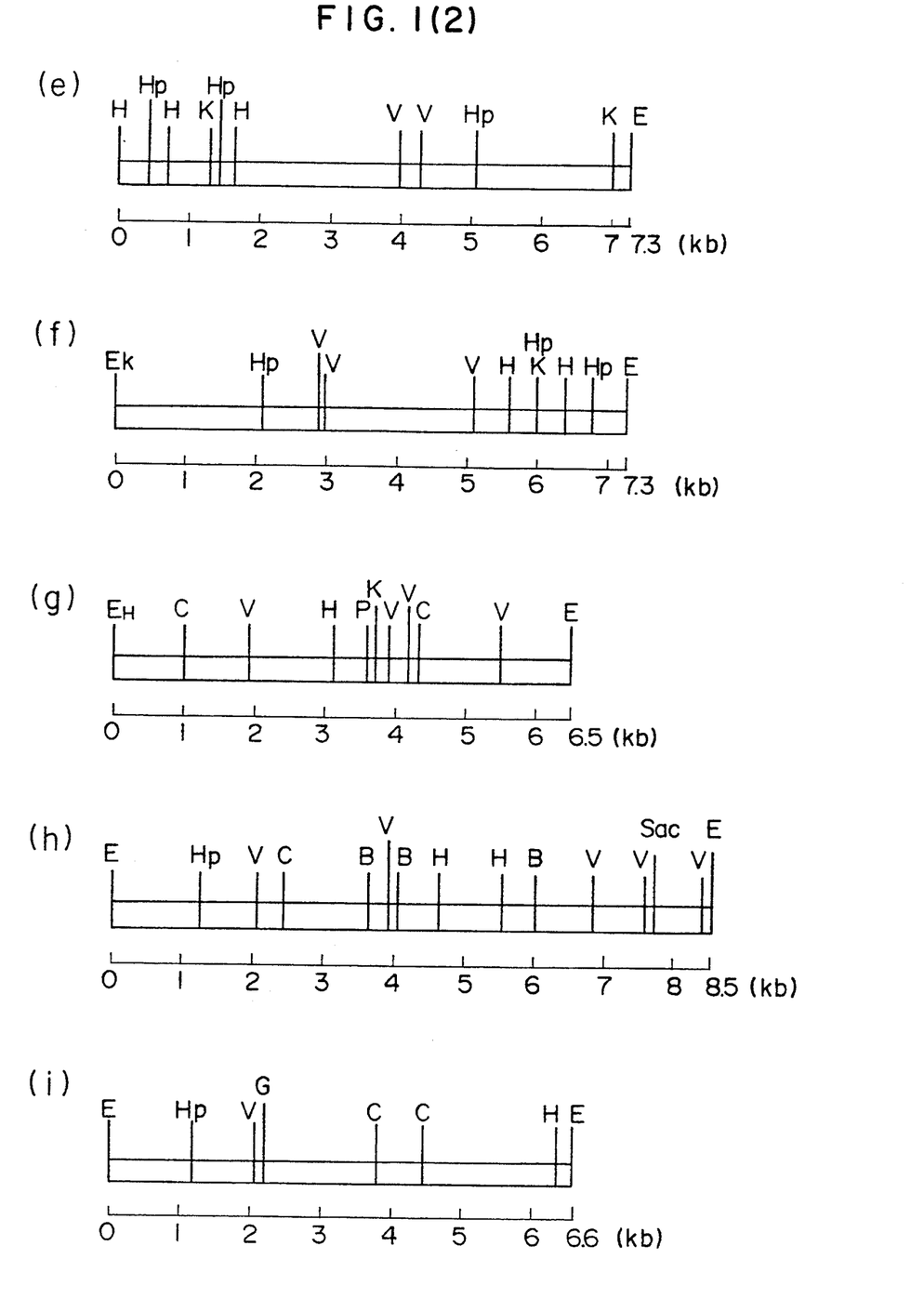
Figure 1I:
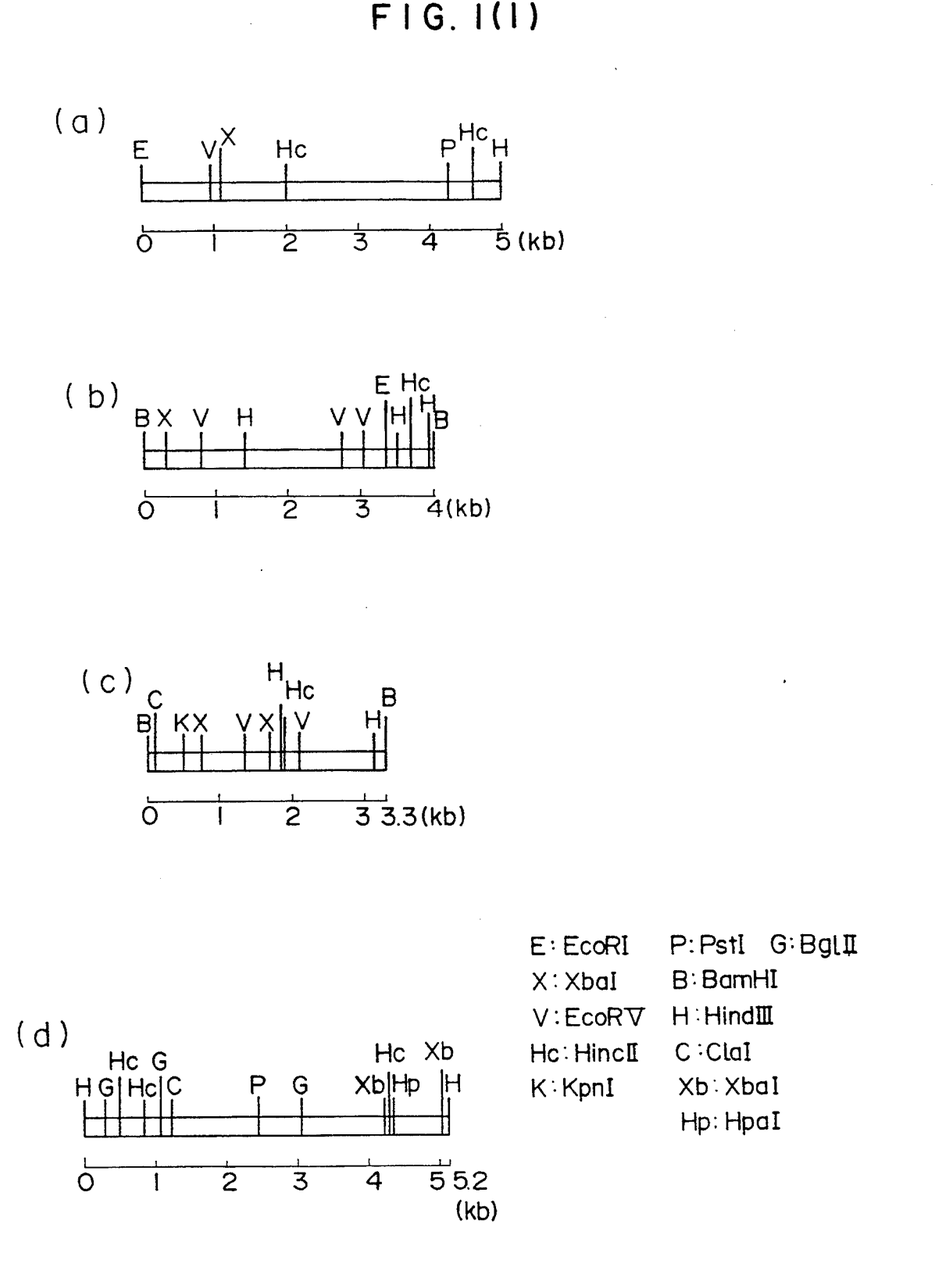

What is claimed is:

1. A recombinant avipoxvirus containing an exogenous DNA under the control of a promoter, said exogenous DNA being inserted into a region non-essential to proliferation of avipoxvirus as a result of homologous recombination with a non-essential region DNA fragment, wherein said non-essential region DNA fragment is a fragment of dovepoxvirus NP having the restriction map shown in FIGS. 1(*a*), (*b*) or (*c*), or a part of said fragment sufficient to undergo homologous recombination with an avipoxvirus.

2. A recombinant avipoxvirus according to claim 1, wherein said avipoxvirus is dovepoxvirus NP strain.

3. A plasmid vector comprising: a dovepoxvirus NP DNA fragment containing a region non-essential to proliferation of avipoxvirus, wherein said fragment has the restriction map shown in FIGS. 1(*a*), (*b*) or (*c*).

4. A plasmid vector as claimed in claim 3 wherein said plasmid vector is pNZ 180, pNZ 160, pNZ 163.

5. A plasmid vector as claimed in claim 3, further comprising an exogenous DNA fragment under the control of a promoter inserted within said dovepoxvirus NP fragment.

6. A plasmid vector according to claim 5, wherein said exogenous fragment is a DNA fragment encoding a detectable enzyme.

7. A plasmid vector according to claim 6 wherein said DNA fragment encoding a detectable enzyme is a DNA fragment encoding β-galactosidase.

8. A plasmid vector according to claim 7, wherein said vector is selected from the group consisting of pNZ 1003, pNZ 1004, and pNZ 1005.

* * * * *